United States Patent
Oesch et al.

(10) Patent No.: US 8,865,422 B2
(45) Date of Patent: Oct. 21, 2014

(54) METHOD FOR THE DIAGNOSIS OF TUBERCULOSIS

(71) Applicant: Prionics AG, Schlieren (CH)

(72) Inventors: Bruno Oesch, Villingen (CH); Irene Schiller, Kilchberg (CH); Martin Vordermeier, Surrey (GB)

(73) Assignee: Prionics AG, Schlieren (CH)

( * ) Notice: Subject to any disclaimer, the term of this patent is extended or adjusted under 35 U.S.C. 154(b) by 0 days.

(21) Appl. No.: 13/718,309

(22) Filed: Dec. 18, 2012

(65) Prior Publication Data

US 2013/0102491 A1 Apr. 25, 2013

Related U.S. Application Data

(62) Division of application No. 12/599,232, filed as application No. PCT/EP2007/004051 on May 8, 2007, now abandoned.

(51) Int. Cl.

| | | |
|---|---|---|
| *G01N 33/00* | (2006.01) | |
| *G01N 33/554* | (2006.01) | |
| *G01N 33/569* | (2006.01) | |
| *C12Q 1/06* | (2006.01) | |
| *C12Q 1/68* | (2006.01) | |
| *G01N 33/53* | (2006.01) | |
| *C12N 1/00* | (2006.01) | |
| *C12N 1/12* | (2006.01) | |
| *C12N 1/20* | (2006.01) | |
| *G01N 33/68* | (2006.01) | |
| *C12Q 1/04* | (2006.01) | |
| *A61K 39/04* | (2006.01) | |

(52) U.S. Cl.
CPC ........ *G01N 33/6854* (2013.01); *G01N 33/5695* (2013.01); *C12Q 1/04* (2013.01); *A61K 39/04* (2013.01)
USPC .......... 435/7.92; 435/7.32; 435/39; 435/6.12; 435/7.1; 435/243; 435/253.1

(58) Field of Classification Search
None
See application file for complete search history.

(56) References Cited

U.S. PATENT DOCUMENTS

| | | | |
|---|---|---|---|
| 6,506,384 B1 * | 1/2003 | Laal et al. | 424/168.1 |
| 2006/0115847 A1 | 6/2006 | Andersen et al. | |
| 2010/0167319 A1 * | 7/2010 | Hope et al. | 435/7.92 |

FOREIGN PATENT DOCUMENTS

| | | |
|---|---|---|
| EP | 0408625 | 7/1996 |
| EP | 0706571 | 9/2004 |
| WO | 02/102409 | 12/2002 |
| WO | 2004/099771 | 11/2004 |
| WO | 2006/117538 | 11/2006 |

OTHER PUBLICATIONS

Molle et al., Molecular Microbiology, 2006; 61(3): 826-837.*
Molle, Virginie et al.; "pH-dependent pore-forming activity of OmpATb from *Mycobacterium tuberculosis* and characterization of the channel by peptidic dissection"; Molecular Microbiology; vol. 61, No. 3; Aug. 2006; pp. 826-837; Blackwell Publishing Ltd.; XP002447469.
Raynaud, Catherine et al.; "The functions of OmpATb, a pore-forming protein of *Mycobacterium tuberculosis* "; Molecular Microbiology, Blackwell Scientific, Oxford, Great Britain; vol. 46, No. 1; Oct. 1, 2002; pp. 191-201; XP002218944.
Bowie et al. (Science, 1990, 257:1306-1310).

* cited by examiner

*Primary Examiner* — Gary Nickol
*Assistant Examiner* — Lakia Tongue
(74) *Attorney, Agent, or Firm* — Rankin, Hill & Clark LLP (57) ABSTRACT

A method for the diagnosis of a tuberculosis infection caused by Mycobacteria belonging to the Mycobacteria tuberculosis complex group (MTC) in an animal including a human being, which comprises in vitro-detection of cell-mediated immune response to OmpAtb and/or antibodies against OmpAtb in a sample taken from that animal.

20 Claims, 6 Drawing Sheets

```
  1 maskaglgqt pattdarrtq kfyrgspgrp wligavvipl liaaigygaf erpqsvtgpt
 61 gvlptltpts trgasalsls llsisrsgnt vtligdfpde aakaalmtal ngllapgvnv
121 idqihvdpvv rsldfssaep vftasvpipd fglkverdtv tltgtapsse hkdavkraat
181 stwpdmkivn nievtgqapp gppasgpcad lqsainavtg gpiafgndga slipadyeil
241 nrvadklkac pdarvtingy tdntgsegin iplsaqraki vadylvargv agdhiatvgl
301 gsvnpiasna tpegraknrr veivvn
```

METHOD FOR THE DIAGNOSIS OF TUBERCULOSIS

CROSS-REFERENCE TO RELATED APPLICATIONS

This application is a division of U.S. application Ser. No. 12/599,232, filed Nov. 6, 2009, which application was filed under 35 U.S.C. §371 as a U.S. National Stage of PCT/EP2007/004051, filed May 8, 2007.

BACKGROUND OF INVENTION

1. Field of Invention

The invention relates to a method for the diagnosis of tuberculosis, especially bovine tuberculosis, by both cellular immune response detection and antibody detection assays in animals including human beings.

2. Description of Related Art

Tuberculosis is caused by Mycobacteria belonging to the Mycobacteria tuberculosis complex group (MTC), which comprises *Mycobacterium tuberculosis* (*M. tuberculosis*), *Mycobacterium bovis* (*M. bovis*), *Mycobacterium caprae* (*M. caprae*), *Mycobacterium africanum* (*M. africanum*), *Mycobacterium microti* (*M. microti*) and *Mycobacterium pinnipedii*.

In methods addressed to by the invention, samples, especially blood samples from a human or an animal are analysed for the presence of a cell-mediated immune response to mycobacterial antigens or of mycobacterial antibodies, respectively, and the presence of a cell-mediated immune response or of antibodies is taken as indication for tuberculosis.

Known methods comprise incubating a blood sample from an animal with mycobacterial antigens, and detecting the presence of cell-mediated immune-response resulting from the incubation or detecting antibodies to mycobacterial antigens, respectively.

EP 0 296 158 discloses a method for the diagnosis of infections including tuberculosis in samples from human or animals. In a first step a whole blood sample from a possibly infected human or animal is incubated with antigens, e.g. a purified tuberculin protein derivative (PPD). After incubation the sample is analysed for the presence of interferon gamma (IFN-γ) released by sensitised lymphocytes to indicate a cell-mediated immune response to the antigen.

PPD has a high sensitivity, its specificity, however, is limited. Therefore, efforts were made to identify further tuberculosis test reagents suited for EP 0 408 625 discloses antibody and cellular assays which use MPB-70 protein from *Mycobacterium bovis* as antigen.

Pub. No. US 2006/0115847 and WO 2006/117538 disclose different peptides, which can be used as antigens in cellular assays and which are mainly selected for their property to distinguish between tuberculosis infection and vaccination with BCG strain.

Finally EP 0 706 571 discloses the use of an antigen called ESAT-6 and WO2004/099771 the use of an antigen called CFP-10 in assays for the diagnosis of tuberculosis.

ESAT-6 and CFP-10 are so far the most immunogenic antigens with superior specificity compared to PPD stimulating in vitro IFN-γ production by T-cells. However, cross-reactivity with *Mycobacterium kansasii* (*M. kansasii*) occurs as ESAT-6 and CFP-10 genes of *M. bovis* and *M. kansasii* are highly identical. *M. kansasii*, not included in the MTC, may be isolated from healthy as well as rarely from diseased individuals and cattle. Management of tuberculosis is often complicated by false interpretation of tests presumptive for MTC.

It has turned out, however that different antigens detect a partially differing population of tuberculosis infected animals. The sensitivity of these antigens appears lower than the sensitivity of tuberculin. As a consequence in some situations, assays using the antigens can produce false negative results.

In view of the above it is an object of the invention to provide an antigen which allows the design of methods for the diagnosis of tuberculosis with increased specificity and, eventually in combination with other antigens, with increased sensitivity.

BRIEF SUMMARY OF THE INVENTION

The object is achieved by a method for the diagnosis of tuberculosis caused by mycobacteria belonging to the MTC, in a susceptible animal a human being, which comprises in vitro-detection of cell-mediated immune response to OmpAtb and/or antibodies against a bacterial outer membrane protein, denominated OmpAtb in a sample.

DETAILED DESCRIPTION OF THE INVENTION

OmpAtb is an outer membrane protein present in e.g. *M. tuberculosis* and *M. bovis*. It forms pores permeable to hydrophilic substances. OmpAtb is highly specific for *M. bovis* and *M. tuberculosis*. Investigations performed by the applicants indicate that OmpAtb is immunogenic in tuberculosis infected cattle. Additionally, tests performed by the applicants revealed that OmpAtb showed a positive reaction in some tuberculosis-positive cases which were tested negative when using ESAT-6 or CFP-10 or a mixture thereof, respectively.

Figure 1:
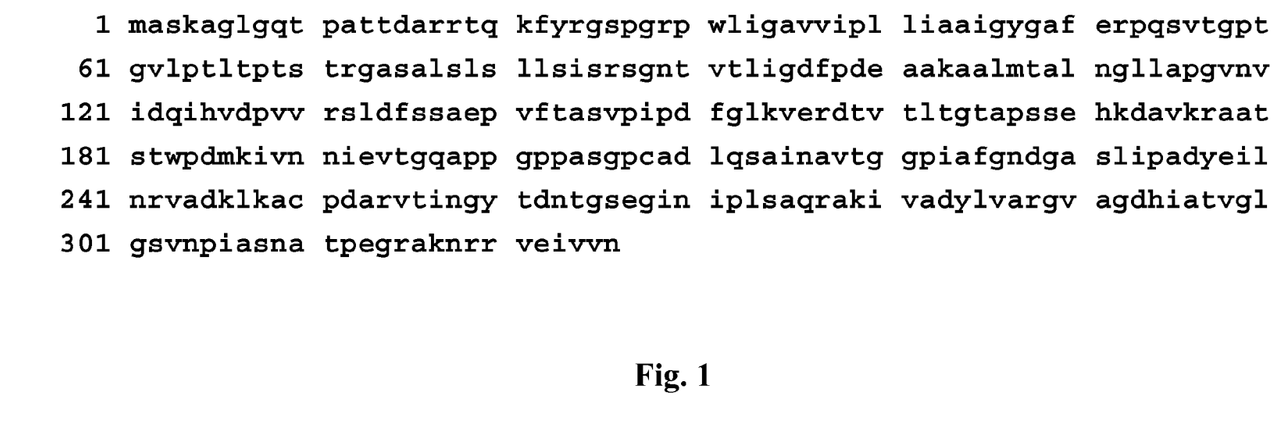
FIG. 1 shows the sequence of OmpAtb (SEQ ID NO: 1).

The sequence of OmpAtb from *M. tuberculosis* H37Rv has been described by Camus et al. (2002) and the sequence of OmpAtb from *M. bovis* AF2122/97 by Garnier et al. (2003). The sequences of OmpAtb in both *M. tuberculosis* and *M. bovis* are identical and an example of the sequence (SEQ ID NO: 1) is shown in FIG. 1.

The function of OmpAtb is associated with its presence in the mycobacterial cell wall. OmpAtb has been found to be a porin-like protein. Its pore-forming activity is pH-dependent, enabling mycobacteria to survive in acidic environmental conditions, such as within macrophage phagosomes (Senaratne et al. 1998, Raynaud et al. 2002, Molle et al. 2006). Up to date, no publication is known to the applicants using immunogenic properties of OmpAtb for the diagnosis of mycobacterial infection.

Preferably the invention is carried out by contacting a blood sample from a tuberculosis-infected animal or human with a test reagent including an antigen having the antigenicity of OmpAtb. It is also possible to use other sample material like e.g. serum, plasma, lymph nodes, skin, saliva, urine, cerebrospinal fluid, and milk to give only some examples. On principle any sample material or tissue, respectively, can be used for analysis which allows the detection of antibodies or a cell mediated immune response upon contact with OmpAtb.

Covered by the present invention is also a skin test which uses OmpAtb or a test reagent including OmpAtb as antigen. Apart from the use of a new antigenic substance any type of skin test for tuberculosis known in the art can be used. The necessary modification or adaptation of the test reagent for use in a skin test is a usual measure for a person skilled in the art and will not be discussed in detail.

In the method according to the invention the antigen or test reagent used can be in solid form or as liquid.

As a rule the sample is collected in a suited sample collecting container like e.g. cell culture vials or a sample collection tube. The antigen or test reagent may be added to the cell culture vial or sample collection tube before or after sample application.

In-tube methods provide that the antigen preparation or test reagent is already contained in the sample collection container used. The advantage is that incubation times are shortened, as the contact of sample and antigen occurs immediately after sample taking when using sample containers with the antigen already included. The invention expressively covers also such methods or sample collection containers.

Throughout the text the term "animal" shall also include human beings. Preferably the method will be used to test cattle as well as all other animal species, e.g. sheep, goats, deer, pigs, horses, badgers, dogs, cats, non-human primates, elephants, opossums, buffaloes, llamas, alpacas and other exotic animals.

Furthermore, in the present context the term "antigenicity" means that the test reagent or the antigen included has the ability of evoking a diagnostically significant immune response either in form of a cell-mediated response or in form of antibodies binding to OmpAtb.

Preferably the antigen is OmpAtb or a peptide subsequence thereof containing the antigenic regions.

The term "OmpAtb" comprises the native form of the protein in mycobacteria as well as recombinant proteins produced in any type of expression vectors transforming any kind of host, and/or also chemically synthesized proteins or peptides. It also includes analogue proteins, i.e. proteins with minor variations not affecting the antigenicity of OmpAtb, e.g. proteins having at least 70% sequence identity to the sequence of OmpAtb. Further included are peptides and fusion proteins including OmpAtb or a subsequence thereof.

By "subsequence" is meant any peptide having an antigenicity comparable to the antigenicity of OmpAtb. The term also encompasses peptide fractions and peptide pools including a number of peptides.

When using peptides or subsequences of OmpAtb, respectively, each of the peptides or subsequence fragments can be present as separate entities or some or all of them are fused together optionally via linkers or spacers such as an amino acid or amino acid sequence.

Fusion-proteins falling under the invention include a polypeptide portion having the antigenicity of OmpAtb and at least one further polypeptide portion. In a preferred embodiment discussed below the further polypeptide portion can have the antigenicity of a further antigen specific for mycobacterial infections. However, it is also possible to provide any further polypeptide portion which improves the properties the fusion protein, as e.g. its selectivity or sensitivity. Also included are polypeptide portions like maltose binding protein, which allow a better isolation of the fusion protein during preparation.

The term "peptide" includes short peptides, oligopeptides and also polypeptides. It comprises native forms of peptides in mycobacteria as well as recombinant peptides and chemically synthesized peptides.

The presence of antibodies to OmpAtb in a sample is detected by testing whether or not a binding reaction of antibodies in the sample with the antigen in the test reagent has occurred. Preferred assays are immunoassays, including enzyme linked immunoassays (ELISA) and immunoblot techniques. However, it is also possible to use non-enzyme linked antibody binding assays, like RIA, fluorescence polarization, flow cytometry and other procedures. Further non-limiting examples for suitable assays are: latex agglutination, lateral flow assay, immunochromatographic assay, immunochips, dip stick immunotesting, bead-based technology in combination with any other method (e.g. chemiluminescence, Luminex), determination of the RNA coding for the relevant cellular product (e.g. cytokine) by use of nucleic acid amplification technique.

A possible cell-mediated immune response can be detected by all suitable methods known in the art. Especially suited are lymphocyte proliferation assays or assays based on release of IFN-γ or other cellular products induced by mycobacterial antigenicity.

Cellular products indicating cell-mediated immune response can be detected by any suite. Non limiting examples for suitable assays are: ELISA, immunoblot techniques, RIA, flow cytometry, fluorescence polarization, latex agglutination, lateral flow assay, immunochromatographic assay, immunochips, dip stick immunotesting, bead-based technology in combination with any other method (e.g. chemiluminescence, Luminex), and determination of the RNA coding for the relevant cellular product by use of nucleic acid amplification technique.

In the antibody detection assays, the antigens used according to the invention may optionally be coupled to solid or semi-solid carriers or be in solution.

Antigens having the antigenicity of OmpAtb especially allow the design of assays with high specificity. In accordance with the invention the sensitivity of the assay may be increased by providing a test reagent including at least one further antigen specific for mycobacterial infections.

The invention also covers a test reagent for the diagnosis of tuberculosis by antibody or cellular assays, including an antigen having the antigenicity of OmpAtb and optionally a further antigen specific for mycobacterial infections.

A preferred test reagent in this context includes the OmpAtb-antigen together with at least one further antigen selected from a group comprising: tuberculin (PPD), ESAT-6, CFP-10, MPB83 (Buddle et al. 2003), TB10.4 (Aagard et al. 2006), TB27.4 (Aagaard et al. 2006), to cite only some examples for preferred antigens. In principle any antigenic peptide or protein specific for tuberculosis can be used as further antigen.

The OmpAtb-antigen and at least one further antigen can be included in form of a mixture in the test reagent. However, in a further preferred embodiment of the invention it is also possible to fuse the antigens in form of a fusion-protein and to include this fusion-protein in the test reagent.

The invention also covers a suitable fusion-protein including a polypeptide portion having the antigenicity of OmpAtb and a further polypeptide portion. Preferably but not necessarily the further polypeptide fraction has the antigenicity of an additional antigen specific for mycobacterial infections.

Furthermore the invention covers a vaccine for immunizing an animal against tuberculosis caused by mycobacteria belonging to the tuberculosis-complex, and comprising as the effective component an antigen with the antigenicity of OmpAtb.

The invention also discloses an improved skin test and a reagent for such a skin test on an animal, including a human being, with the composition mentioned above.

Finally the invention is directed to a kit for the diagnosis or exclusion of a tuberculosis infection caused by mycobacteria belonging to the MTC in a sample taken from an animal, which comprises the test reagent as described above and means for the detection of antibodies against OmpAtb and/or means for the detection of a cell-mediated immune response to OmpAtb by the animal.

EXAMPLES

Figure 4:
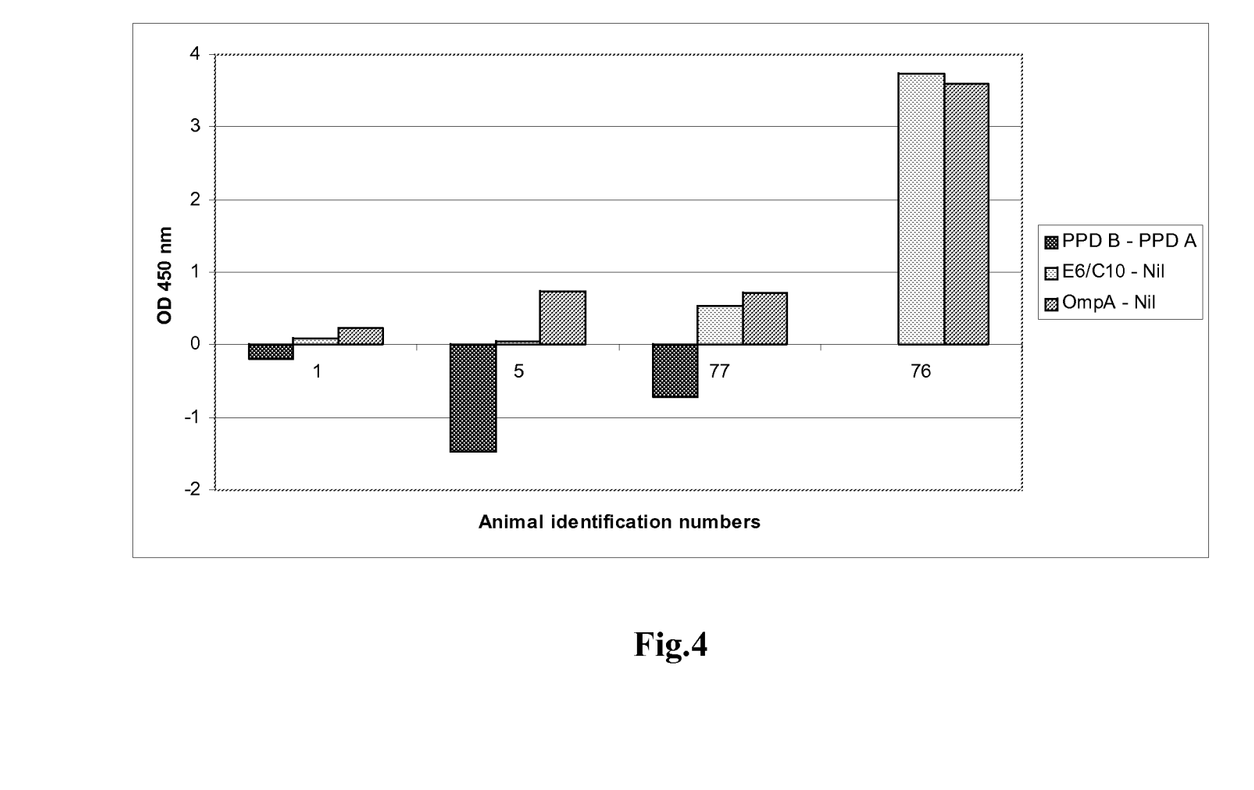
FIG. 4 is a graph showing animal identification numbers from use of specified antigens as well as OmpAtb in an assay analysing tuberculosis-infected cattle reacting false negative with PPDs as described in Example 3 below.
Figure 5:
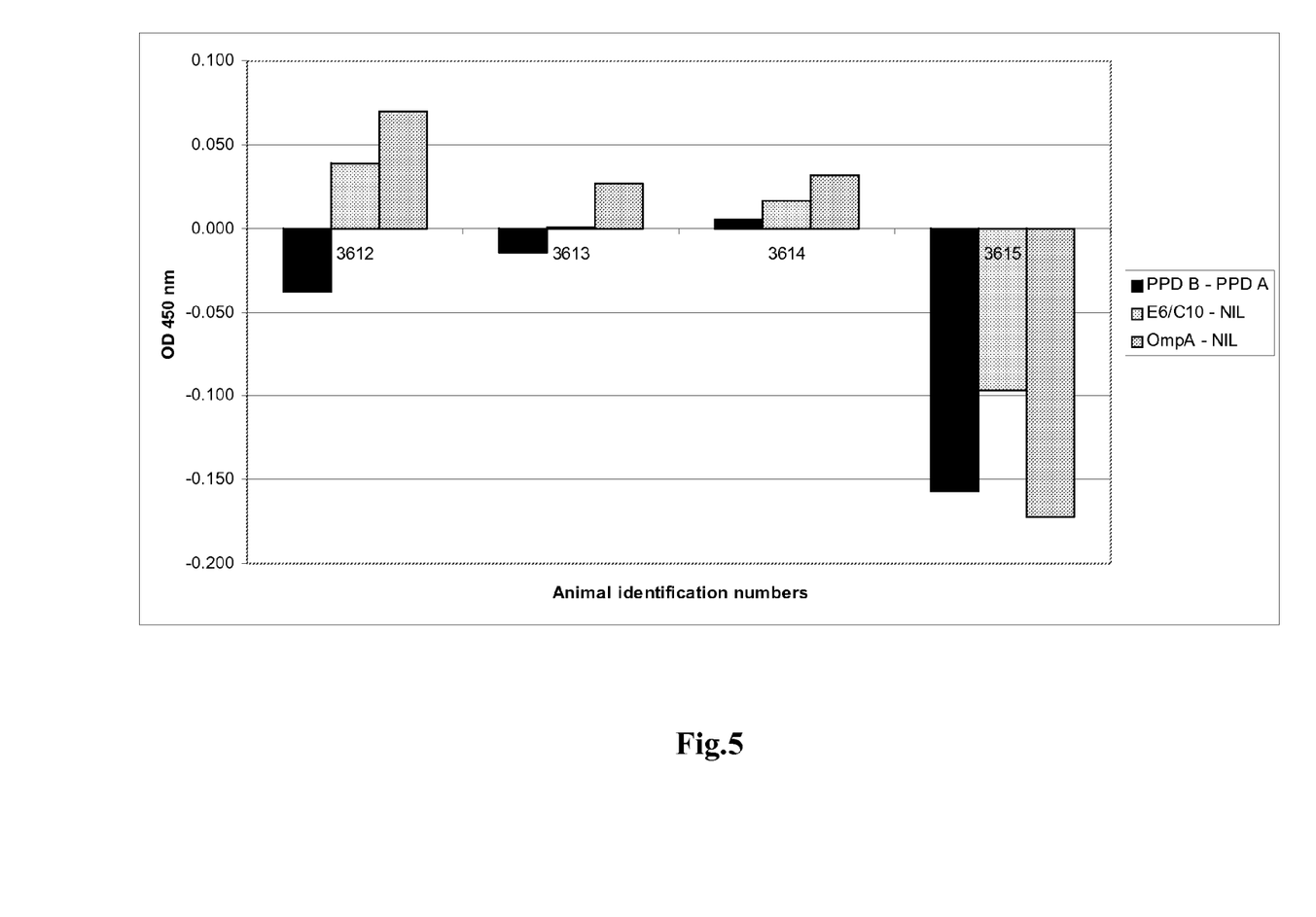
FIG. 5 is a graph showing animal identification numbers from use of specified antigens as well as OmpAtb in an assay analysing non-infected cattle as described in Example 4 below.
Figure 6:
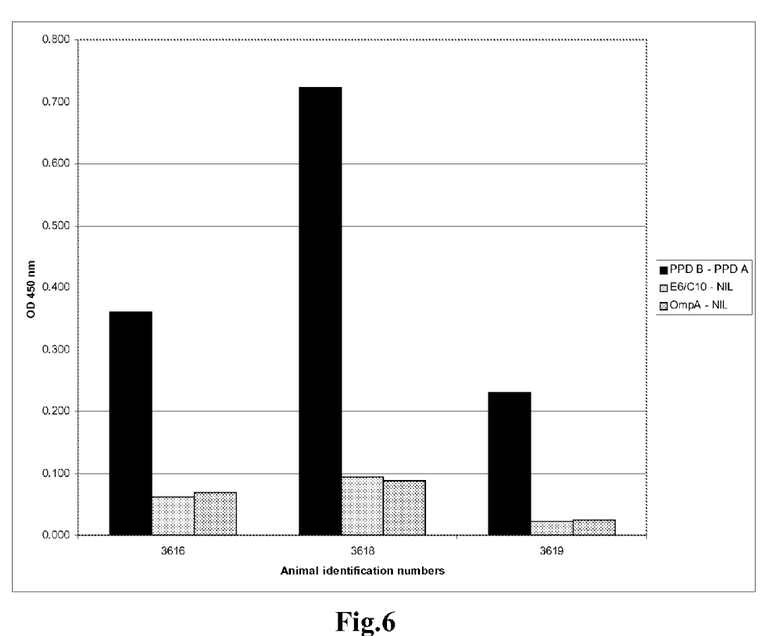
FIG. 6 is a graph showing animal identification numbers from use of specified antigens as well as OmpAtb in an assay analysing non-infected cattle reacting false positive with PPDs as described in Example 5 below.

The following examples demonstrate the preferred use of OmpAtb in assays analysing tuberculosis-infected cattle (FIGS. 2, 3, 4) and non-infected cattle (FIGS. 5 and 6).

The different examples represent different classes of animals. Example 1 refers to tuberculosis-infected animals positive with PPDs and other antigens as well as with OmpAtb (FIG. 2) showing that OmpAtb is equal to other methods in these animals. Example 2 refers to tuberculosis-infected animals reacting false negative with ESAT6/CFP10 (FIG. 3) but correctly diagnosed with OmpAtb. Example 3 refers to tuberculosis-infected animals being false negative with PPDs (FIG. 4) but correctly diagnosed with OmpAtb. Example 4 refers to animals negative for tuberculosis (FIG. 5) and Example 5 to non-infected animals false positive with PPDs (FIG. 6) but correctly diagnosed with OmpAtb.

Example 1

Comparative Testing of Naturally Infected Animals Responding to ESAT-6 and CFP-10

Animals and Samples

Blood samples were collected in heparinized tubes from 4 skin test (comparative cervical tuberculin test) positive cattle. The animals were of Holstein Friesian breed and 13 to 15 months old.

Antigens

OmpAtb was obtained from a commercial source (Proteix, Prague, Czech Republic). A truncated version of the protein was produced according to Senaratne et al. (1998) as a fusion protein with the maltose binding protein. After synthetic gene synthesis, DNA fragments were inserted into BstBl site of pET28b-MalE expression vector at the C-terminus of MalE protein. Large-scale production was performed in *E. coli* BL24 lambda DE3.

OmpAtb was used at a concentration of 5 µg/ml in whole blood culture.

Purified protein derivate from *M. bovis* (PPD-B) or from *M. avium* (PPD-A) was used at a concentration of 10 µg/ml. PPD-B and PPD-A were obtained from the Veterinary Laboratory Agency, Weybridge, UK.

Peptides between 16 and 20 amino acids in length were synthesized and formulated into an ESAT-6/CFP-10 peptide cocktail as described by Cockle et al. 2002 and used at a concentration of 5 µg/ml/peptide.

Maltose binding protein purchased from Proteix (Prague, Czech Republic) at a concentration of 5 µg/ml and medium (RPMI, Invitrogen/Gibco, Basel, Switzerland) were used for stimulation as negative controls.

Staphylococcal enterotoxin B (Sigma), 1 µg/ml, was used as positive control.

Cultures

Cultures were set up within 5 hrs after blood collection. 250 µl of whole blood per well were established in 96-well microtitre plates and stimulated by the addition of antigens. The supernatants were harvested after 24 hrs of culture at 37° C. and 5% $CO_2$ in a hunified incubator.

IFN-γ ELISA

The IFNγ concentration in culture supernatants was measured using the BOVIGAM ELISA kit (Prionics AG, Zurich, Switzerland). Optical density was determined at 450 nm ($OD_{450}$). A positive result was defined as: $OD_{450}$ PPD-B minus PPD-A=0.1 and $OD_{450}$ PPD-B minus Nil=0.1 $OD_{450}$ Antigens minus Nil=0.1.

Results

Figure 2:
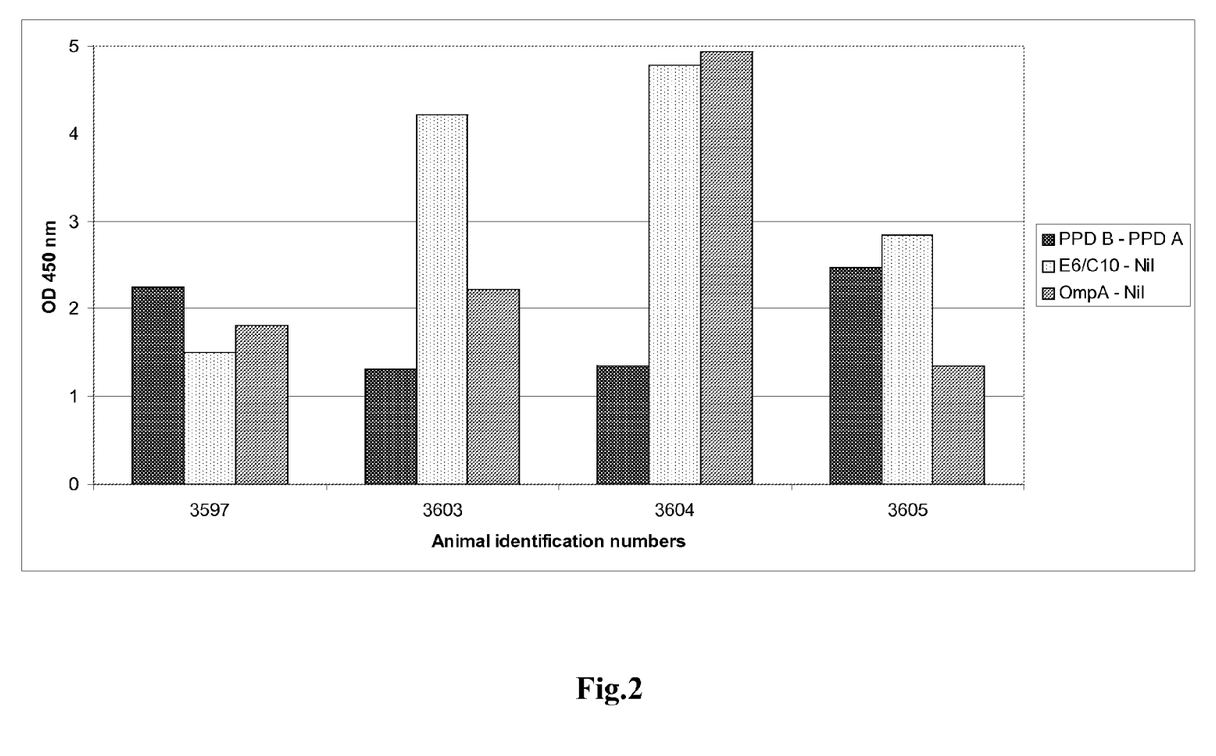
FIG. 2 is a graph showing animal identification numbers from use of specified antigens as well as OmpAtb in an assay analysing tuberculosis-infected cattle as described in Example 1 below.

All animals reacted clearly positive with PPDs, ESAT-6/CFP-10 and OmpA used as stimulating antigens. The results of Nil corrected OD values (ESAT-6/CFP-10 and OmpA) and OD PPD-B minus PPD-A values are shown in FIG. 2.

Example 2

Comparative Testing of Naturally Infected Animals not Responding to ESAT-6 and CFP-10

Animals and Samples

Blood samples were collected in heparinized tubes from 4 skin test (comparative cervical tuberculin test) positive cattle. The animals were of Holstein Friesian breed and 13 to 15 months old.

Antigens were the same as described in Example 1. Cultures and IFN-γ ELISA procedures were performed as described in Example 1.

Results

Figure 3:
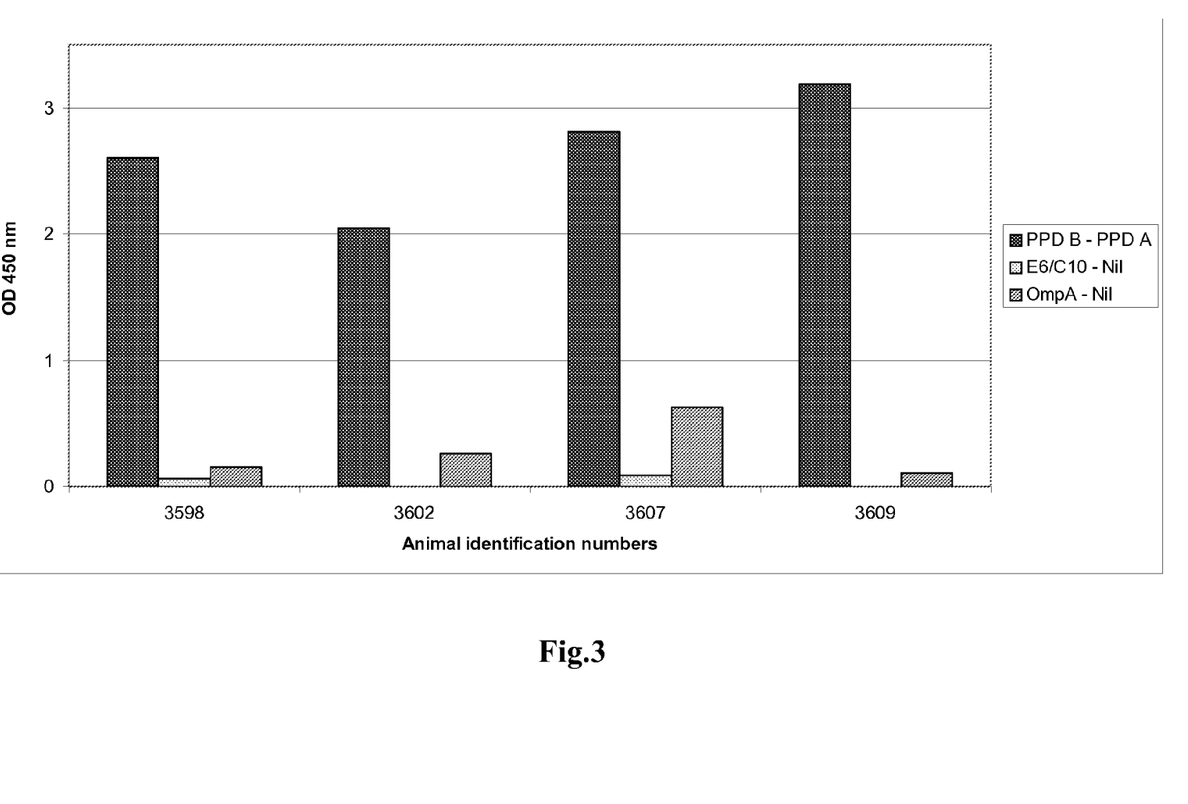
FIG. 3 is a graph showing animal identification numbers from use of specified antigens as well as OmpAtb in an assay analysing tuberculosis-infected cattle reacting false negative with ESATg/CFP10 as described in Example 2 below.

All animals reacted clearly positive with PPDs. Due to a low PPD-A response in these animals the OD values of PPD-B corrected by PPD-A are at a high level. ESAT-6/CFP-10 responses were in all 4 cattle below the cut off. OmpA reaction however was positive (FIG. 3).

Example 3

Comparative Testing of Experimentally Infected Animals Reacting False Negative with PPDs Animals and Samples Five cattle were infected with $10^5$ CFU of *M. bovis* strain 95-1315. They were 6 months old, of Holstein Friesian breed. Blood samples were collected in heparinized tubes 14 days post infection (animals 1, 5, 77) and 29 days post infection (animal 76).

Antigens

OmpAtb was the same as described in Example 1.

ESAT-6/CFP-10 was constructed as fusion protein according to Waters et al. 2004.

PPD-B and PPD-A were obtained from Prionics AG (Zurich, Switzerland) and used at a concentration of 20 μg/ml. Pokeweed mitogen (Sigma), 10 μg/ml, was used positive control for stimulation.

Cultures and IFNγ ELISA procedures were performed as described in Example 1.

Results

All animals reacted false negative with PPDs due to PPD-A responses exceeding the PPD-B reactivity. ESAT-6/CFP-10 was below cut off in animals 1 and 5, and positive in cattle 77 and 76. OmpA gave positive results in all 4 cattle (FIG. 4).

Example 4

Comparative Testing of Tuberculosis Negative Animals

Animals and Samples

Whole blood was taken from 7 tuberculosis negative cattle. The animals were of Holstein Friesian breed and about 12 months old.

Antigens were the same as described in Example 1. Cultures and IFNγ ELISA procedures were performed as described in Example 1.

Results

Four animals (FIG. 5) were negative with all antigens. Three cattle (FIG. 6), however, reacted false positive with PPDs but negative with ESAT-6/CFP-10 and OmpA.

What is claimed:

1. A method for diagnosing a tuberculosis infection in an animal caused by Mycobacteria belonging to the *Mycobacteria tuberculosis* complex group, the method comprising:
   acquiring sample material or tissue from the animal from which the detection of antibodies or a cell mediated immune response upon contact with OmpAtb can be detected upon analysis;
   contacting the sample material or tissue acquired from the animal with a test reagent comprising an antigen having antigenicity of OmpAtb; and
   detecting in vitro the presence or absence of antibodies to OmpAtb or a cell mediated immune response to OmpAtb in the sample material or tissue contacted with the test reagent;
   wherein the presence of antibodies to OmpAtb or a cell-mediated immune response to OmpAtb in the sample material or tissue contacted with the test reagent constitutes a positive diagnosis of a tuberculosis infection in the animal from which the sample material or tissue was acquired caused by Mycobacteria belonging to the *Mycobacteria tuberculosis* complex group, and
   wherein the absence of antibodies to OmpAtb or a cell-mediated immune response to OmpAtb in the sample material or tissue contacted with the test reagent constitutes a negative diagnosis of a tuberculosis infection in the animal from which the sample material or tissue was acquired caused by Mycobacteria belonging to the *Mycobacteria tuberculosis* complex group.

2. The method according to claim 1, wherein the antigen having antigenicity of OmpAtb is OmpAtb.

3. The method according to claim 2, wherein the test reagent further comprises at least one further mycobacterial antigen.

4. The method according to claim 3, wherein the at least one further mycobacterial antigen is selected from the group consisting of tuberculin (PPD), ESAT-6, CFP-10, MPB83, TB10.4 and TB27.4.

5. The method according to claim 1, wherein the test reagent comprises the antigen having antigenicity of OmpAtb in form of a fusion-protein.

6. The method according to claim 5, wherein the fusion protein further comprises at least one further mycobacterial antigen.

7. The method according to claim 6, wherein at least one further mycobacterial antigen is selected from the group consisting of tuberculin (PPD), ESAT-6, CFP-10, MPB83, TB10.4 and TB27.4.

8. The method according to claim 1, wherein the animal is selected from the group consisting of humans, cattle, sheep, goats, deer, pigs, horses, badgers, dogs, cats, non-human primates, elephants, opossums, buffaloes, llamas, alpacas.

9. The method according to claim 1, wherein the sample material or tissue is selected from the group consisting of blood, serum, plasma, lymph nodes, skin, saliva, urine, cerebrospinal fluid and milk.

10. The method according to claim 1, wherein a cell-mediated immune response to OmpAtb is detected in the assay based on release of gamma interferon or other cellular products signaling mycobacterial immunity.

11. The method according to claim 1, wherein a cell-mediated immune response to OmpAtb is detected in the assay based on lymphocyte proliferation.

12. The method according to claim 10, wherein the other cellular products indicating a cell-mediated immune response to OmpAtb are detected by one of the following:
   ELISA;
   immunoblot techniques;
   RIA;
   flow cytometry;
   fluorescence polarization;
   latex agglutination;
   lateral flow assay;
   immunochromatographic assay;
   immunochips;
   dip stick immunotesting;
   bead-based technology; and
   determination of RNA coding by use of a nucleic acid amplification technique.

13. The method according to claim 1, wherein the presence of antibodies to OmpAtb in the sample material or tissue contacted with the test reagent is detected by determining whether a binding reaction of antibodies in the sample material or tissue with the antigen having antigenicity of OmpAtb in the test reagent has occurred.

14. The method according to claim 13, wherein the binding reaction is detected by one of the following:
   ELISA;
   immunoblot techniques;
   RIA;
   flow cytometry;
   fluorescence polarization;
   latex agglutination;
   lateral flow assay;
   immunochromatographic assay;
   immunochips;
   dip stick immunotesting;
   bead-based technology; and
   determination of RNA coding by use of a nucleic acid amplification technique.

15. A method for diagnosing tuberculosis infections in cattle caused by Mycobacteria belonging to the Mycobacteria tuberculosis complex group, the method comprising:
- acquiring individual blood samples from the cattle;
- contacting the individual blood samples acquired from the cattle with a test reagent comprising an antigen having antigenicity of OmpAtb; and
- detecting in vitro the presence or absence of antibodies to OmpAtb or a cell mediated immune response to OmpAtb in the individual blood samples contacted with the test reagent;
- wherein the presence of antibodies to OmpAtb or a cell-mediated immune response to OmpAtb in the individual blood samples contacted with the test reagent constitutes a positive diagnosis of a tuberculosis infection caused by Mycobacteria belonging to the Mycobacteria tuberculosis complex group in the cattle from which the individual blood samples were acquired, and
- wherein the absence of antibodies to OmpAtb or a cell-mediated immune response to OmpAtb in the individual blood samples contacted with the test reagent constitutes a negative diagnosis of a tuberculosis infection caused by Mycobacteria belonging to the Mycobacteria tuberculosis complex group in the cattle from which the individual blood samples were acquired.

16. The method according to claim 15, wherein the test reagent further comprises at least one further mycobacterial antigen.

17. The method according to claim 16, wherein the at least one further mycobacterial antigen is selected from the group consisting of tuberculin (PPD), ESAT-6, CFP-10, MPB83, TB10.4 and TB27.4.

18. The method according to claim 15, wherein the individual blood samples acquired from the cattle are collected in sample collection tubes.

19. The method according to claim 18, wherein the sample collection tubes contain the test reagent comprising the antigen having antigenicity of OmpAtb before the individual blood samples are collected therein.

20. The method according to claim 15, wherein the presence or absence of antibodies to OmpAtb or a cell-mediated immune response to OmpAtb in the individual blood samples contacted with the test reagent is determined via ELISA or an immunoblot technique.

\* \* \* \* \*

SEQUENCE LISTING

```
<160> NUMBER OF SEQ ID NOS: 1

<210> SEQ ID NO 1
<211> LENGTH: 326
<212> TYPE: PRT
<213> ORGANISM: Mycobacterium tuberculosis

<400> SEQUENCE: 1

Met Ala Ser Lys Ala Gly Leu Gly Gln Thr Pro Ala Thr Thr Asp Ala
1               5                   10                  15

Arg Arg Thr Gln Lys Phe Tyr Arg Gly Ser Pro Gly Arg Pro Trp Leu
                20                  25                  30

Ile Gly Ala Val Val Ile Pro Leu Leu Ile Ala Ala Ile Gly Tyr Gly
            35                  40                  45

Ala Phe Glu Arg Pro Gln Ser Val Thr Gly Pro Thr Gly Val Leu Pro
        50                  55                  60

Thr Leu Thr Pro Thr Ser Thr Arg Gly Ala Ser Ala Leu Ser Leu Ser
65                  70                  75                  80

Leu Leu Ser Ile Ser Arg Ser Gly Asn Thr Val Thr Leu Ile Gly Asp
                85                  90                  95

Phe Pro Asp Glu Ala Ala Lys Ala Ala Leu Met Thr Ala Leu Asn Gly
            100                 105                 110

Leu Leu Ala Pro Gly Val Asn Val Ile Asp Gln Ile His Val Asp Pro
        115                 120                 125

Val Val Arg Ser Leu Asp Phe Ser Ser Ala Glu Pro Val Phe Thr Ala
    130                 135                 140

Ser Val Pro Ile Pro Asp Phe Gly Leu Lys Val Glu Arg Asp Thr Val
145                 150                 155                 160

Thr Leu Thr Gly Thr Ala Pro Ser Ser Glu His Lys Asp Ala Val Lys
                165                 170                 175

Arg Ala Ala Thr Ser Thr Trp Pro Asp Met Lys Ile Val Asn Asn Ile
            180                 185                 190

Glu Val Thr Gly Gln Ala Pro Pro Gly Pro Pro Ala Ser Gly Pro Cys
        195                 200                 205

Ala Asp Leu Gln Ser Ala Ile Asn Ala Val Thr Gly Gly Pro Ile Ala
    210                 215                 220

Phe Gly Asn Asp Gly Ala Ser Leu Ile Pro Ala Asp Tyr Glu Ile Leu
225                 230                 235                 240

Asn Arg Val Ala Asp Lys Leu Lys Ala Cys Pro Asp Ala Arg Val Thr
                245                 250                 255

Ile Asn Gly Tyr Thr Asp Asn Thr Gly Ser Glu Gly Ile Asn Ile Pro
```

-continued

```
                260                 265                 270
Leu Ser Ala Gln Arg Ala Lys Ile Val Ala Asp Tyr Leu Val Ala Arg
            275                 280                 285

Gly Val Ala Gly Asp His Ile Ala Thr Val Gly Leu Gly Ser Val Asn
        290                 295                 300

Pro Ile Ala Ser Asn Ala Thr Pro Glu Gly Arg Ala Lys Asn Arg Arg
305                 310                 315                 320

Val Glu Ile Val Val Asn
                325
```